United States Patent [19]

Kowligi et al.

[11] Patent Number: 5,152,782
[45] Date of Patent: Oct. 6, 1992

[54] NON-POROUS COATED PTFE GRAFT

[75] Inventors: Rajagopal R. Kowligi, Tempe; Robert C. Farnan, Tucson; William M. Colone, Phoenix; Linda V. Della Corna, Glendale; Joseph B. Sinnott, Mesa, all of Ariz.

[73] Assignee: Impra, Inc., Tempe, Ariz.

[21] Appl. No.: 358,011

[22] Filed: May 26, 1989

[51] Int. Cl.⁵ ............................................. A61F 2/06
[52] U.S. Cl. ....................................................... 623/1
[58] Field of Search ............................... 623/1, 11, 12

[56] References Cited

U.S. PATENT DOCUMENTS

| | | | |
|---|---|---|---|
| Re. 31,618 | 7/1984 | Mano et al. | 3/1.4 |
| 3,279,996 | 10/1966 | Long et al. | 167/82 |
| 3,479,670 | 11/1969 | Medell | 3/1 |
| 3,585,647 | 6/1971 | Gajewski et al. | 3/1 |
| 3,646,616 | 3/1972 | Keshin | 623/12 |
| 4,011,861 | 3/1977 | Enger | 128/2.06 |
| 4,173,689 | 11/1979 | Lyman et al. | 521/64 |
| 4,187,390 | 2/1980 | Gore | 7/18 |
| 4,193,138 | 3/1980 | Okita | 3/1.4 |
| 4,194,041 | 3/1980 | Gore et al. | 428/315 |
| 4,208,745 | 5/1980 | Okita | 3/1.4 |
| 4,304,010 | 12/1981 | Mano | 3/1.4 |
| 4,306,318 | 12/1981 | Mano et al. | 3/1.4 |
| 4,321,711 | 3/1982 | Mano | 3/1.4 |
| 4,344,999 | 8/1982 | Gohlke | 428/212 |
| 4,355,426 | 10/1982 | MacGregor | 3/1.4 |
| 4,377,010 | 4/1983 | Fydelor et al. | 3/1.4 |
| 4,441,215 | 4/1984 | Kaster | 3/1.4 |
| 4,657,544 | 4/1987 | Pinchuk | 623/1 |
| 4,718,907 | 1/1988 | Karwoski et al. | 623/12 |
| 4,743,258 | 5/1988 | Ikada et al. | 623/1 |
| 4,784,659 | 11/1988 | Fleckenstein et al. | 623/12 |
| 4,816,339 | 3/1989 | Tu et al. | 428/421 |
| 4,851,009 | 7/1989 | Pinchuk | 623/1 |
| 4,872,867 | 10/1989 | Joh | 623/11 |
| 4,902,290 | 2/1990 | Fleckenstein et al. | 623/1 |

FOREIGN PATENT DOCUMENTS 0157178 10/1985 European Pat. Off.
2077107A 12/1981 United Kingdom.

OTHER PUBLICATIONS

Sugarman, "In Vitro Adherence of Bacteria to Prosthetic Vascular Grafts"; *Infection*, 1982, 10:1-12.
Rosenman, et al., "Bacterial Adherence to Vascular Grafts After In Vitro Bacteremia", *Journal of Surgical Research*, vol. 38, 648-655 (1985).
Schmitt, et al., "Mucin Production By Staphylococcus Epidermidis", *Arch. Surg.*, vol. 121, Jan. 1986, pp. 89-95.
Schmitt, et al., "Bacterial Adherence to Vascular Prostheses: A Determinant of Graft Infectivity", *Journal of Vascular Surgery*, vol. 3, No. 5, May 1986, pp. 732-740.
An In Vitro Study of the Properties Influencing Staphylococcus Epidermidis Adhesion to Prosthetic Vascular Graft Materials, Joel M. Harris, M.D., and Louis F. Martin, M.D., Ann. Surg. Nov. 1987, pp. 612-619.
Promotional Literature for "Tecoflex" by Thermedics, Inc., Tecoflex Solution Processible Grades, 470 Wildwood St., Woburn, Mass.
Kenney et al., "Evaluation of Compliant and Noncompliant PTFE Vascular Prostheses", *Trans Am. Soc. Artif. Intern. Organs*, vol. XXXIV, 1988, pp. 661-663.
Shu et al., "Flow Phenomena in Compliant and Noncompliant Arterioenous Grafts", *Trans. Am. Soc. Artif. Intern. Organs*. vol. XXXIV, 1988, pp. 519-523.

*Primary Examiner*—David Isabella
*Attorney, Agent, or Firm*—Cahill, Sutton & Thomas

[57] ABSTRACT

A non-porous coated PTFE graft includes a PTFE tube having a conventional porous inner cylindrical wall and a non-porous elastomeric coating applied over at least a portion of the outer cylindrical wall of the PTFE tube to render such portion of the outer cylindrical wall non-porous. The elastomeric coating is made of polyurethane or another biocompatible non-porous elastomer and precludes tissue ingrowth into the outer cylindrical wall, minimizes suture hole bleeding, and increases suture retention strength, while reducing the incidence of serous weepage. The elastomeric coating is preferably applied by mounting the PTFE tube upon a mandrel of like diameter and either dip coating or spray coating all, or selected portions, of the PTFE tube with liquified polyurethane. After the polyurethane coating is completely dried, the non-porous vascular graft is removed form the mandrel and is ready for use.

9 Claims, 2 Drawing Sheets

NON-POROUS COATED PTFE GRAFT

CROSS-REFERENCE TO RELATED PATENT APPLICATIONS

1. "BLOOD VESSEL PATCH", Ser. No. 07/358,785, filed concurrently herewith, naming Berguer et al. as inventors, and assigned to the assignee of the present invention.

2. "LONGITUDINALLY COMPLIANT PTFE GRAFT", Ser. No. 07/358,011, filed concurrently herewith, naming Della Corna et al. as inventors, and assigned to the assignee of the present invention, now issued as U.S. Pat. No. 4,955,899.

BACKGROUND OF THE INVENTION

1. Field of the Invention

The present invention relates generally to prosthetic vascular grafts for implantation within the vascular system of a patient, and more particularly, to a prosthetic vascular graft made from expanded, porous polytetrafluoroethylene (PTFE) tubing that is fabricated to retain the porous inner cylindrical wall of conventional PTFE vascular grafts, but wherein the outer cylindrical wall of the PTFE tube is rendered non-porous over at least a portion of its length.

2. Description of the Prior Art

The use of implantable prosthetic vascular grafts made of expanded, porous PTFE is well known in the art. Such vascular grafts are often implanted just below the skin to provide blood access for long term hemodialysis. Such PTFE vascular grafts are also used to replace or bypass occluded or damaged natural blood vessels. Such prosthetic vascular grafts, and methods of implanting the same, are generally described in Bennion et al., "Hemodialysis and Vascular Access", *Vascular Surgery*, pp. 625-662, 1983. Methods of forming expanded, porous PTFE tubing are well known in the art. For example, U.S. Pat. No. 4,187,390 issued to Gore discloses one such process which may be used to produce highly porous, expanded PTFE structures.

Expanded, porous PTFE material offers a number of advantages when used as a prosthetic vascular graft. PTFE is highly biocompatible, has excellent mechanical and handling characteristics, does not require pre-clotting with the patient's blood, heals relatively quickly following implantation, and is thromboresistant. Notwithstanding its many advantages, certain problems may arise with the use of PTFE vascular grafts. For example, PTFE material is not very elastic, and the suture holes formed in the ends of the graft when the graft is sutured to a blood vessel during implantation often leak blood until clotting occurs within the suture holes. Moreover, while porous PTFE vascular grafts are generally impermeable to blood, instances have arisen wherein serous weepage has occurred; serous weepage arises when the watery portion of the blood passes through the wall of the PTFE vascular graft and forms a collection of fluid, known as a seroma, adjacent the outer wall of the vascular graft. Additionally, instances have arisen wherein sutures used to secure the ends of PTFE vascular grafts to blood vessels within the body have torn the wall of the PTFE vascular graft, causing failure thereof.

Conventional PTFE vascular grafts have a porous outer cylindrical wall which facilitates tissue ingrowth into the outer cylindrical wall of the vascular graft, thus helping to heal and stabilize the graft. Nonetheless, there are instances wherein it is desired to preclude such tissue ingrowth. For example, should it later become necessary to perform a thrombectomy to remove a blood clot within the graft, the wall of the graft must be exposed in order to permit the formation of an incision therein. Exposure of the vascular graft is made more difficult if significant tissue ingrowth has taken place. Similarly, there are instances wherein it is desired to implant a jump graft onto a previously existing vascular graft. Once again, the outer cylindrical wall of the original graft must be exposed in order to implant the jump graft. However, the significant tissue ingrowth fostered by conventional PTFE vascular grafts make such exposure more difficult.

Accordingly, it is an object of the present invention to provide a PTFE vascular graft having a porous inner cylindrical wall and including an outer cylindrical wall, at least a portion of which is rendered non-porous for preventing tissue ingrowth and facilitating later exposure of the vascular graft.

It is another object of the present invention to provide such a PTFE vascular graft which eliminates or minimizes suture hole bleeding when the graft is implanted.

It is still another object of the present invention to provide such a PTFE vascular graft which significantly reduces the incidence of serous weepage.

It is a further object of the present invention to provide such a PTFE vascular graft with increased suture retention strength to avoid tearing of the walls of the graft.

These and other objects of the present invention will become more apparent to those skilled in the art as the description thereof proceeds.

SUMMARY OF THE INVENTION

Briefly described, and in accordance with the preferred embodiments thereof, the present invention relates to a PTFE vascular graft having a porous inner cylindrical wall and having an opposing outer cylindrical wall, wherein at least a portion of the outer cylindrical wall is rendered non-porous through the application of a non-porous elastomeric coating thereto. The vascular graft includes an expanded, porous PTFE tube, and a coating of a non-porous elastomer coated to at least a portion of the outer cylindrical wall of the PTFE tube. The coated portion of the PTFE tube precludes tissue ingrowth into the outer cylindrical wall thereof, minimizes blood leakage through any suture holes formed therein, increases suture retention strength, while reducing the incidence of serous weepage.

Non-porous polyurethane is preferably used to form the non-porous elastomeric coating upon the outer cylindrical wall of the PTFE tube. Other biocompatible elastomers which may be used to form such coating include medical-grade silicone rubber elastomers, segmented polyurethanes, polyurethane-ureas, and silicone-polyurethane copolymers.

PTFE vascular grafts can be formed with the above-described non-porous elastomeric coating applied over the entire length of the underlying PTFE tube. Alternatively, the non-porous elastomeric coating may be applied over the outer cylindrical wall of the PTFE tube only along the first and second opposing end portions of the PTFE tube, and not along the central portion thereof. Such end-coated PTFE vascular grafts provide the aforementioned advantages of minimizing suture hole bleeding, increased suture retention strength, and preclude tissue ingrowth near the points of anastomosis, while permitting tissue ingrowth in the central portion of the vascular graft to help stabilize the same.

The present invention also relates to the method by which such implantable vascular grafts may be produced. The porous PTFE tube starting material is coated with a liquified elastomer upon at least a portion of the outer cylindrical wall thereof, and the liquified elastomeric coating is then dried to form the non-porous coating upon the outer cylindrical wall of the PTFE tube. As used herein, the term liquified elastomer should be understood to refer to an elastomer dissolved in a liquid solvent. Preferably, the PTFE tube starting material is pulled over a cylindrical mandrel having an outer diameter commensurate with the internal diameter of the PTFE tube, before the liquified elastomeric coating is applied. The liquified elastomer is preferably applied by either dip coating or spray coating the liquified elastomer upon the PTFE tube while the PTFE tube is supported upon the mandrel. Those portions, if any, of the outer cylindrical wall of the PTFE tube which are to remain porous are not coated with the liquified elastomer.

DETAILED DESCRIPTION OF THE PREFERRED EMBODIMENTS

Figure 1:
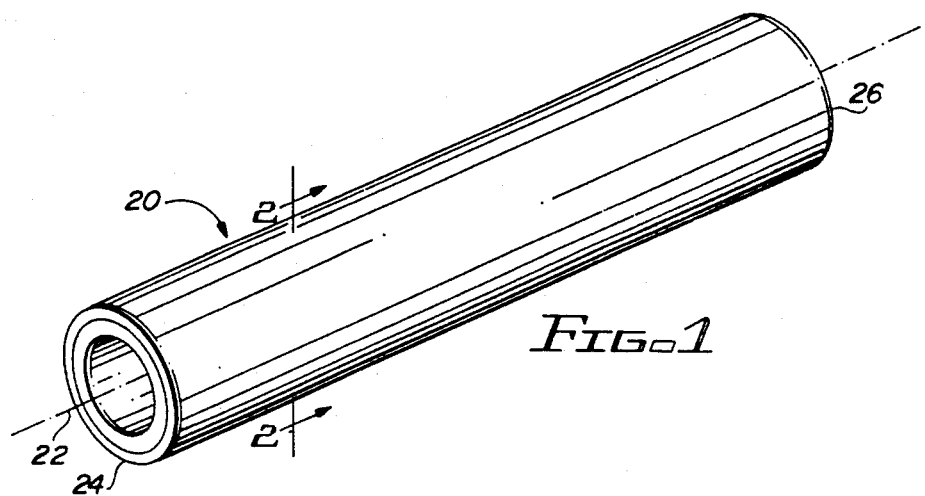
FIG. 1 is a perspective view of a PTFE vascular graft and including a non-porous outer cylindrical wall in accordance with one of the preferred embodiments of present invention.

In FIG. 1, a PTFE vascular graft having a non-porous outer cylindrical wall is designated generally by reference numeral 20. As shown, vascular graft 20 is in tubular form and may be made to have any desired length and internal diameter. Within FIG. 1, dashed lines 22 indicate the central longitudinal axis of vascular graft 20. Vascular graft 20 includes a first end 24 and an opposing second end 26.

Figure 2:
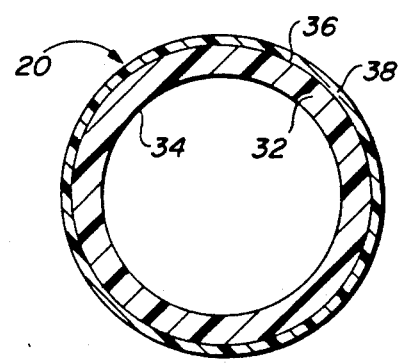
FIG. 2 is a cross-sectional drawing of the non-porous PTFE vascular graft shown in FIG. 1 and taken through lines 2—2 as designated within FIG. 1.

Within FIG. 2, a cross section of vascular graft 20 is shown. Vascular graft 20 includes an inner expanded, porous PTFE tube 32 having a micro-structure characterized by nodes interconnected by fibrils. PTFE tube 32 includes an inner cylindrical wall 34 and an opposing outer cylindrical wall 36. As shown in FIG. 2, outer cylindrical wall 36 is coated entirely around its circumference by a uniformly thick coating 38 of a biocompatible elastomer.

The preferred starting material used to form PTFE tube 32 is expanded porous PTFE material of the type generally described within U.S. Pat. No. 4,187,390 to Gore. Such expanded, porous PTFE material is commonly used to form prosthetic vascular grafts. The preferred wall thickness of PTFE tube 32 ranges from 0.1 millimeter to 1.0 millimeters; the preferred internodal distance within such expanded PTFE material ranges from 10 micrometers to 60 micrometers. The longitudinal tensile strength of such PTFE material is preferably equal to or greater than 1500 psi, and the radial tensile strength of such PTFE material is preferably equal to or greater than 400 psi. The suture retention strength of such PTFE starting material is preferably equal to or greater than 300 grams.

In regard to elastomeric coating 38 shown in FIG. 2, such elastomeric coating is selected to be a biocompatible elastomer and may be selected from the group consisting of medical-grade silicone rubber elastomers, segmented polyurethanes, polyurethane-ureas, and silicone-polyurethane copolymers. Suitable candidates for use as elastomeric coating 38 typically have a hardness rating between 50A-100A and 55D-60D. Most of the above-mentioned elastomers can be chemically or biologically modified to improve biocompatability; such modified compounds are also candidates for use in forming elastomeric coating 38 shown in FIG. 2.

Apart from biocompatability, other requirements of an elastomer to be a suitable candidate for use as elastomeric coating 38 are that the elastomer be sufficiently elastic to effect instantaneous closure of suture holes formed by a suture needle. Elasticity should be balanced against the thickness of elastomeric coating 38, the objective being to select the minimum coating thickness necessary to prevent significant blood leakage through the suture hole locations without significantly impeding suture needle penetration. The elastomeric coating should also be sufficiently non-porous to preclude serous weepage and inhibit tissue ingrowth therethrough. Yet another requirement of such elastomers is that they be easily dissolvable in low boiling point organic solvents such as tetrahydrofuran, methylene chloride, trichloromethane, dioxane, and dimethylflormamide, by way of example. Finally, suitable elastomers should lend themselves to application to PTFE tube 32 by either the dip coating or spray coating methods described in greater detail below.

The presently preferred elastomer used to form elastomeric coating 38 is a polyurethane formulation grade SG-80 sold under the trademark "TECOFLEX" by Thermedics, Inc. of Woburn, Mass. Such formulations are considered medical grade aliphatic polyurethanes resins of solution processible grades. Such formulations are designed to be dissolved in various solvents for use in solution casting or for coating of medical products. The polyurethane formulation is preferably dissolved in the solvent known as Tetrahydrofuran (THF), a solvent commercially available from Mallinckrodt, Inc. through the Scientific Products Division of Baxter Corp., of Irvine, Calif.

Further details concerning the preferred construction of vascular graft 20 shown in FIGS. 1 and 2 can more readily be understood in conjunction with the preferred method by which vascular graft 20 is produced. It has already been noted above that PTFE tube 32 is formed of expanded, porous PTFE material of a type often used to form vascular prostheses. In practicing the preferred method, the PTFE starting material is initially in the form of a cylindrical tube having an inside diameter ranging from 1.0 millimeters to 30 millimeters, and ranging in length up to 100 centimeters.

Figure 6:
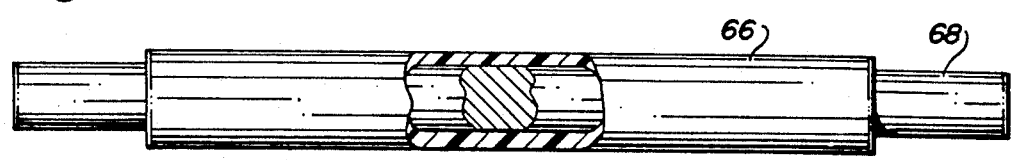
FIG. 6 is a top view of a PTFE tube pulled onto a supporting mandrel prior to being coated with a liquified elastomer.

Prior to applying the non-porous elastomeric coating to the outer cylindrical walls of the PTFE tube, the PTFE tube is preferably pulled onto a supporting mandrel, as shown in FIG. 6. Within FIG. 6, the PTFE tube starting material is designated by reference numeral 66. As shown in FIG. 6, PTFE tube 66 is pulled over a cylindrical supporting mandrel 68 which has an outer diameter that is equal to or slightly larger than the internal diameter of PTFE tube 66. Preferably, mandrel 68 should be approximately 0.2-0.4 millimeters larger than the inside diameter of PTFE tube 66 to prevent PTFE tube 66 from sliding upon the mandrel during coating.

After mounting PTFE tube 66 upon mandrel 68, the above-described elastomeric coating may then be applied to the outer cylindrical wall of PTFE tube 66. As mentioned above, the two preferred methods of applying the elastomeric coating are dip coating and spraying. Regardless of which application method is used, the preferred method of formulating the liquified elastomer is the same. As has been described, the preferred liquified elastomer is formed by preparing a solution of "Tecoflex" polyurethane grade SG-80A. This solution is prepared by dissolving polyurethane pellets in the above-described terahydrofuran solvent in a heated glass reactor equipped with a cold water condenser held at 60° C. Such polyurethane pellets may also be dissolved in the solvent at room temperature through continuous stirring. The use of the heated reactor is preferred, as it dissolves the polyurethane pellets in a few hours, whereas the method of stirring the solution at room temperature takes approximately two days.

The preferred solids content for "Tecoflex" grade SG-80A is 2-4 percent by weight; however, the solids content may range up to 15 percent by weight, depending upon the specific polymer composition, the dip coating parameters, and the intended end uses. Where multiple coatings are employed, the composition of the polyurethane solution may be varied between coating layers. For example, it might be advantageous to apply progressively more dilute polyurethane solutions to the underlying PTFE tube.

Following preparation of the liquified polyurethane solution as described above, the next step is to apply the polyurethane solution as a coating upon the outer wall of PTFE tube 66. The method of dip coating the PTFE tube will now be described in conjunction with FIG. 4, which illustrates a dip coating machine.

Figure 4:
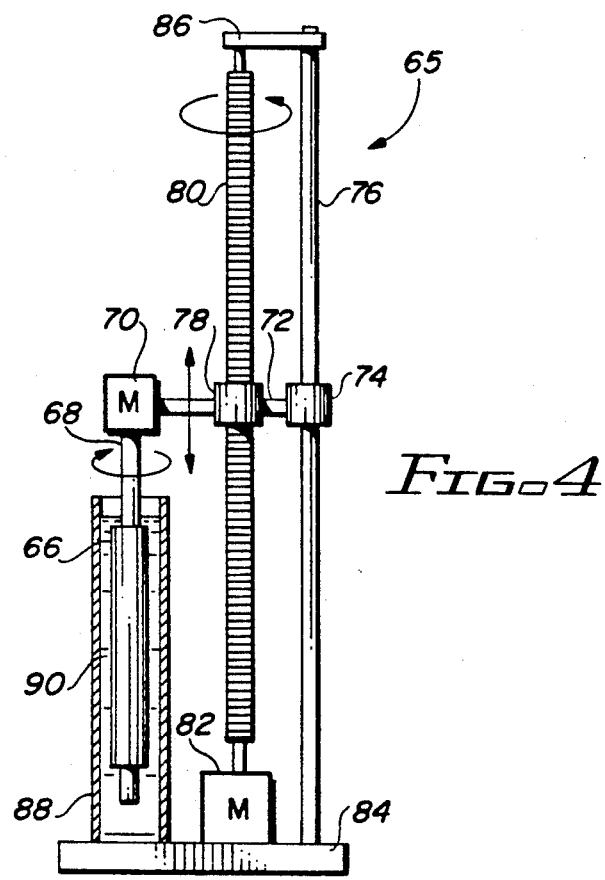
FIG. 4 is a front view of a dip coating apparatus adapted to apply a uniform elastomeric coating to the outer cylindrical wall of a PTFE tube.

FIG. 4 illustrates a dip coating machine designated generally by reference numeral 65. As mentioned above, mandrel 68 is preferably selected to have a diameter that is approximately 0.2-0.4 millimeters larger than the inside diameter of PTFE tube 66 to prevent PTFE tube 66 from sliding upon mandrel 68 during the coating process. Preferably, the length of PTFE tube 66 is approximately 25-30 centimeters. Lengths in excess of 30 centimeters are not preferred due to the effects of gravity pulling upon the polyurethane coating during the coating process; attempts to process PTFE tube sections much in excess of 25-30 centimeters in length can result in uneven coating thicknesses as measured between the top and bottom of mandrel 68.

As shown in FIG. 4, mandrel 68 extends vertically downward from a motor 70 which continuously rotates mandrel 68 and PTFE tube 66 secured thereto. Motor 70 is, in turn, supported by a bracket 72 adapted to travel vertically upward and downward. Bracket 72 includes a smooth bushing 74 through which a smooth vertical support rod 76 passes. Bushing 74 is adapted to slide upwardly and downwardly along support rod 76. Bracket 72 further includes a threaded collar 78 through which a threaded rotatable drive rod 80 passes. The lowermost end of drive rod 80 is secured to the drive shaft of a second motor 82 which rotates in a first rotational direction to raise mandrel 68 and which rotates in an opposing rotational direction to lower mandrel 68. Both motor 82 and support rod 76 are supported at their lower ends by a base 84. The upper end of support rod 76 is fixedly secured to bracket 86 which rotatably supports the upper end of drive rod 80.

Motor 82 of dip coating machine 65 is initially operated to raise mandrel 68 to its uppermost position. A tall, slender container 88 containing the above-described polyurethane solution 90 is placed upon base 84 immediately below mandrel 68. Motor 82 may then be operated in the reverse rotational direction to lower mandrel 68, and PTFE tube section 66 secured thereto, into polyurethane solution 90.

The variables controlled by dip coating machine 65 include the speed at which mandrel 68 is immersed and withdrawn, the rotational speed of mandrel 68, and the drying time between successive coatings. These parameters are controlled to ensure that the polymer coating penetration is restricted to the outer layers of the PTFE tube section 66.

The preferred number of polyurethane solution coatings applied to PTFE tube 66 is eight, but may range between one and twenty coatings, depending upon the concentration of the elastomer solution used in the dipping process, and depending upon the intended use of the end product. The preferred coating thickness at the completion of the dip coating process is between 0.06-0.08 millimeters, but may vary up to two millimeters, depending upon the dimensions of the coated tube and the elastomer solution concentration.

The dip coating procedure of immersing and then withdrawing PTFE tube 66 is a continuous process, and PTFE tube 66 is continuously in motion at any given time during the procedure. Drying intervals between successive polyurethane coatings can vary up to a few hours depending upon the type of solvent used and the drying conditions. PTFE tube 66 is dried in ambient air, preferably in an inert atmosphere, but may also be dried at elevated temperatures of 40°-100° C. PTFE tube 66 remains secured to mandrel 68 until the coating and drying process described above is completed. When the last of the eight coatings has substantially dried, PTFE tube 66 is further dried under vacuum at 50° C. at 10-15 mmHg vacuum for 10-24 hours to completely remove any remaining solvents. The polyurethane coated PTFE tube is then removed from mandrel 68.

A second method for applying the polyurethane coating to the PTFE tube involves the use of spraying and will now be described in conjunction with the spray coating machine shown in FIG. 5. The polyurethane solution to be sprayed is first prepared in the same manner as described above for the dip coating process. The polyurethane solution is inserted within cylinder 92 of a pump 94 for delivery through a plastic tube 96 to a spray nozzle 98. An inert gas, such as nitrogen, is also supplied to spray nozzle 98 through connecting tube 100 from supply tank 102. An inert gas is preferably used to minimize reactions which polyurethane can undergo upon exposure to air and oxygen.

Figure 5:
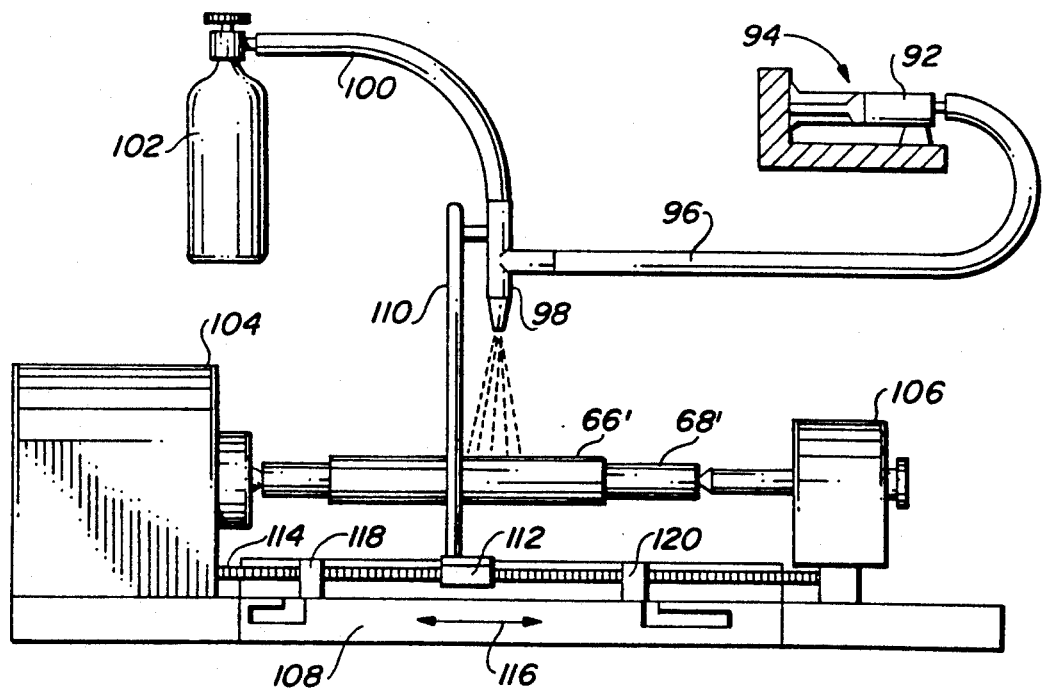
FIG. 5 is a front view of a spray coating apparatus which may be used to spray a liquified elastomer upon the outer cylindrical wall of a PTFE tube to form a uniform elastomeric coating thereupon.

Still referring to FIG. 5, PTFE tube 66' is again stretched over a mandrel 68'. Once again, mandrel 68' is preferably of a diameter slightly larger than the inner diameter of PTFE tube 66' to prevent PTFE tube 66' from sliding thereupon. Mandrel 68' is supported for rotation about a horizontal axis. One end of mandrel 68' is coupled to the drive shaft of a first motor (not shown) within motor housing 104, while the opposite end of mandrel 68 is rotatably supported by bracket 106. Both motor housing 104 and bracket 106 are supported upon base 108. The aforementioned first motor continuously rotates mandrel 68' at speeds of up to 500 rotations per minute.

Spray nozzle 98 is supported for reciprocal movement above and along mandrel 68'. As shown in FIG. 8, spray nozzle 98 is secured to support rod 110 which includes at its lowermost end a carriage 112. A threaded drive rod 114 is coupled at a first end to the drive shaft of a second motor (not shown) within motor housing 104 for being rotated thereby. The opposite end of threaded drive rod 114 is supported by and freely rotates within bracket 106. Threaded drive rod 114 threadedly engages a threaded collar (not shown) within carriage 112. Accordingly, rotation of drive rod 114 causes carriage 112, and hence spray nozzle 98, to move in the directions designated by dual headed arrow 116, depending upon the direction of rotation of drive rod 114. Also shown in FIG. 5 are a pair of microswitches 118 and 120 which are periodically engaged by carriage 112 and which, when actuated, reverse the direction of rotation of threaded drive rod 114 in a manner which causes spray nozzle 98 to reciprocate back and forth along mandrel 68'.

As shown in FIG. 5, spray nozzle 98 makes several passes along mandrel 68', repetitively spraying PTFE tube 66' as it rotates. Spray nozzle 98 is caused to travel at a linear speed of up to 50 centimeters per minute. The polyurethane coating thickness which results from this spraying process is determined by the speed of rotation of mandrel 68', the linear speed of spray nozzle 98, as well as the rates of delivery of both the polyurethane solution by pump 94 and the rate of delivery of inert gas. These rates of delivery may range up to 5 milliliters per minute for the polyurethane solution, and up to 5 liters per minute for the nitrogen gas. After an appropriate number of spray cycles, PTFE tube 66' is vacuum dried and pulled from mandrel 68', in the same manner as described above.

While the dip coating and spray coating methods described above in conjunction with FIGS. 4 and 5 are directed to the process of coating the entire outer cylindrical wall of the PTFE tube 66, those skilled in the art will appreciate that such dip coating and spray coating methods may be used to form a non-porous elastomeric coating upon only portions of the PTFE tube. For example, it may be desired to provide a PTFE vascular graft 40 like that shown in FIG. 3 wherein only the opposing end portions 42 and 44 of vascular graft 40 are to have a non-porous outer cylindrical wall. Accordingly, the dip coating process illustrated in FIG. 4 may be practiced by dipping only one end of PTFE tube 66 (corresponding to first end 42 of graft 40 in FIG. 3) into the liquified polyurethane solution 90; after the desired number of coatings have been applied to the lower end of PTFE tube 66, mandrel 68 may be inverted to cause the opposite end of PTFE tube 66 (corresponding to second end 44 of graft 40 in FIG. 3) to be immersed within polyurethane solution 90. Similarly, in FIG. 5, spray nozzle 98 may be maintained away from the central region of PTFE tube 66' to avoid spraying such central region with the liquified elastomer. Alternatively, a cylindrical shield (not shown) may be extended around the central portion of PTFE tube 66' within the spray coating apparatus of FIG. 5 to prevent the liquified polyurethane spray from contacting the central region of PTFE tube 66'.

With respect to the end-coated PTFE vascular graft described above in conjunction with FIG. 3, a cross section taken through either of end portions 42 or 44 would resemble the cross-sectional drawing shown in FIG. 2. The central portion of graft 40 in FIG. 3 extending between end portions 42 and 44 would have a cross section as shown in FIG. 2, but without the elastomeric coating 38. Within FIG. 3, the central portion of graft 40 has been shown as being of reduced outer diameter in comparison with the outer diameters of end portions 42 and 44, for purposes of illustration. In most instances, the actual variation in wall thickness along the length of graft 40 would be difficult to detect visibly. The preferred dimensions of the end-coated sections 42 and 44 may range up to 40 percent of the overall length of the graft. The extent of the coating will depend upon the specific application and surgeon preference. A short coated length may be preferred when only the advantages of reduced suture hole bleeding and increased suture retention strength are sought. A longer coated length may be desired to allow for more trimming of the ends of the graft, and/or to reduce tissue ingrowth to a greater extent at the ends of the graft. Briefly referring to FIG. 4, the lengths of the end portions of the graft shown in FIG. 3 are easily adjusted by controlling the depth of immersion of PTFE tube 66 into polyurethane solution 90.

Figure 3:
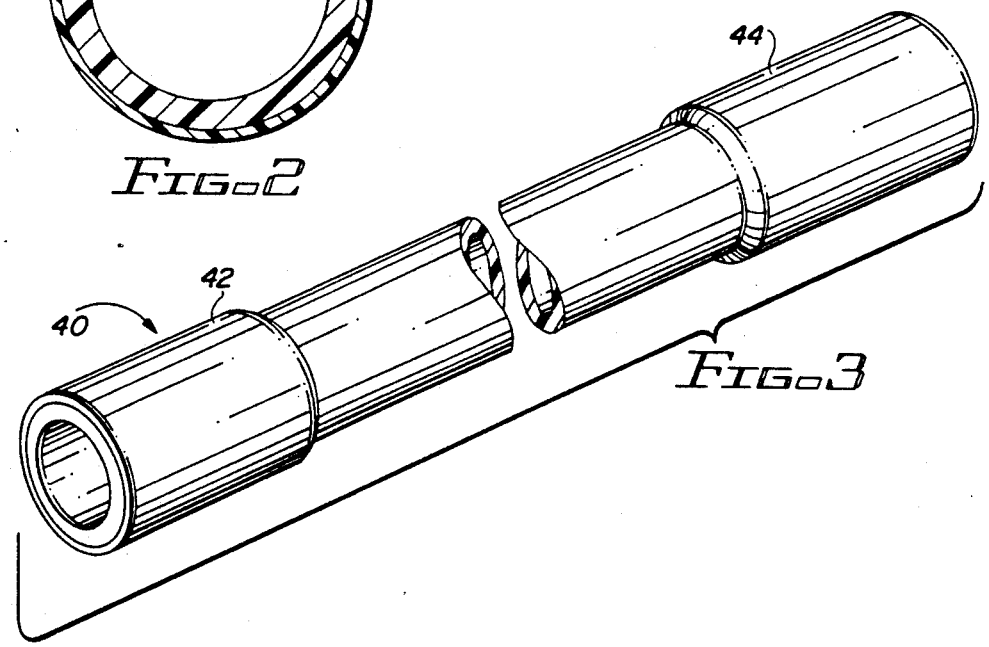
FIG. 3 is a perspective view of an alternate embodiment of the present invention wherein only the opposing end portions of the PTFE vascular graft are rendered non-porous.

Apart from the fully-coated and end-coated vascular grafts shown in FIGS. 1 and 3, respectively, other configurations of non-porous coated PTFE grafts may also be constructed. For example, it might be desired to provide a PTFE graft wherein only the central portion of the graft is coated with polyurethane or another biocompatible elastomer.

A laboratory simulation was conducted in a manner described below to determine the susceptibility of non-porous coated PTFE vascular grafts to suture hole bleeding. Test segments were taken from two PTFE tube sections, each measuring 19 millimeters in internal diameter, one of such tube sections being pure PTFE having a wall thickness of 0.774 millimeters and the second PTFE tube section having a wall thickness of 0.594 millimeters and having a polyurethane coating thickness of 0.088 millimeters applied to it in the manner described above. Thus, the overall wall thickness of the coated test segments was less than that of the uncoated test segments. A two inch length from each of the aforementioned tube sections was clamped between two hemostats, and ten 6-0 polypropylene sutures were placed in a continuous fashion in the middle of each tube. The test sections were then each pressurized to 2 psi with water, and water loss through the suture holes was measured for a one minute period. Similar measurements were also made with the water pressure being raised to 4 psi. Leak rate measurements obtained by the procedure described above are set forth below.

| Water Pressure (Psi) | Leak Rate (ml/min) | |
| --- | --- | --- |
| | Non-coated PTFE Tube | Coated PTFE Tube |
| 2 psi | 11.04 | 3.44 |
| 4 psi | 19.96 | 8.3 |

By way of comparison, normal blood pressures within the human body typically range from 1.8 to 2.3 psi. Thus, the formation of the polyurethane coating upon the PTFE tube significantly reduces the suture hole leakage rate.

The aforementioned laboratory simulation was also used to compare suture retention strength of such non-porous coated PTFE vascular grafts to conventional uncoated PTFE vascular grafts. Both axial suture retention strength and radial suture retention strength were tested. Axial suture retention strength was tested by sewing a 6-0 polypropylene suture through the wall of the graft two millimeters from the end and applying a load to the suture along the longitudinal axis of the tubular graft. Peak loads at failure of the graft or breaking of the suture itself were noted. Radial suture retention strength was tested by first slitting the tubular test segment, opening the test segment to form a relatively flat sheet, sewing 6-0 polypropylene suture into the test segment, and applying a load to the suture in a direction perpendicular to what would have been the longitudinal axis of the tubular graft before it was slit open. Again, peak loads at failure of the graft or breaking of the suture itself were noted. The results of this comparison are set forth below:

| Axial and Radial Suture Retention Strength | | |
| --- | --- | --- |
| | Non-coated PTFE Tube | Coated PTFE Tube |
| Axial suture retention strength (grams) | 321.4 ± 63.4 | 747.1 ± 169.3 |
| Radial suture retention strength (grams) | 782.2 ± 74.3 | 743.9 ± 80.3 |

Thus, the polyurethane coating significantly increases axial suture retention strength without adversely impacting upon radial suture retention strength.

The aforementioned laboratory simulation also included a comparative investigation of the respective water entry pressures for the uncoated and coated PTFE test segments described above. Water entry pressure is a test of the pressure at which water applied to the inner passageway of the graft leaks through the outer porous wall of the PTFE tube, and thereby serves as a measure of the tendency for such a vascular graft to exhibit serous weepage when implanted in the body. The respective water entry pressures noted for the test segments described above are as follows.

| Water Entry Pressure | | |
| --- | --- | --- |
| | Non-coated PTFE Tube | Coated PTFE Tube |
| Water entry pressure (psi) | 7.4 ± 0.76 | >15 psi |

Thus, the polyurethane coating significantly increases water entry pressure and lessens the tendency of a graft to exhibit serous weepage.

Those skilled in the art will now appreciate that an improved PTFE vascular graft has been described which has a cylindrical outer wall that is non-porous over at least a portion of its length and which may be used wherever prosthetic vascular grafts are currently used today, including various applications in both peripheral vascular and vascular access uses. The above-described graft may be implanted in the same manner as is currently used to implant porous PTFE vascular grafts. Moreover, the elastomeric coating minimizes suture hole bleeding at the time of implantation, increases suture retention strength, reduces serous weepage, and selectively precludes tissue ingrowth at the coated sections. While the invention has been described with reference to preferred embodiments thereof, the description is for illustrative purposes only and is not to be construed as limiting the scope of the invention. Various modifications and changes may be made by those skilled in the art without departing from the true spirit and scope of the invention as defined by the appended claims.

We claim:

1. An implantable vascular graft comprising:
   a. an expanded, porous PTFE tube having inner and outer cylindrical walls; and
   b. a non-porous coating of a non-porous elastomer applied over at least a portion of the outer cylindrical wall of said PTFE tube, said coating having a substantially uniform thickness.

2. The implantable vascular graft recited by claim 1 wherein said non-porous elastomer coating is a coating of non-porous polyurethane.

3. The implantable vascular graft recited by claim 1 wherein said elastomer is selected from the group of elastomers consisting of medical-grade silicone rubber elastomers, segmented polyurethanes, polyurethane-ureas, and silicone-polyurethane copolymers.

4. An implantable vascular graft comprising:
   a. an expanded, porous PTFE tube having inner and outer cylindrical walls, and having first and second opposing end portions and a central portion lying between said first and second opposing end portions; and
   b. a non-porous coating of a non-porous elastomer applied over the outer cylindrical wall of said PTFE tube along said first and second opposing end portions but not along the central portion of said PTFE tube.

5. The implantable vascular graft recited by claim 4 wherein said non-porous elastomer coating is a coating of non-porous polyurethane.

6. The implantable vascular graft recited by claim 4 wherein said elastomer is selected from the group of elastomers consisting of medical-grade silicone rubber elastomers, segmented polyurethanes, polyurethane-ureas, and silicone-polyurethane copolymers.

7. An implantable vascular graft comprising:
   a. an expanded, porous PTFE tube having inner and outer cylindrical walls;
   b. a non-porous coating of a non-porous elastomer applied over at least a portion of the outer cylindrical wall of said PTFE tube but not to the inner cylindrical wall of said PTFE tube, said coating having a substantially uniform thickness; and
   c. the inner cylindrical wall of said PTFE tube being uncoated and porous.

8. The implantable vascular graft recited by claim 7 wherein said non-porous elastomer coating is a coating of non-porous polyurethane.

9. The implantable vascular graft recited by claim 7 wherein said elastomer is selected from the group of elastomers consisting of medical-grade silicone rubber elastomers, segmented polyurethanes, polyurethane-ureas, and silicone-polyurethane copolymers.

* * * * *